United States Patent [19]

Mayer et al.

[11] 4,017,500

[45] Apr. 12, 1977

[54] CERTAIN 8-AMINO-1,7-NAPHTHYRIDINES

[75] Inventors: Joseph Mayer, New York, N.Y.; Margaret H. Sherlock, Bloomfield, N.J.

[73] Assignee: Schering Corporation, Kenilworth, N.J.

[22] Filed: Nov. 12, 1975

[21] Appl. No.: 631,010

Related U.S. Application Data

[60] Division of Ser. No. 379,525, July 16, 1973, Pat. No. 3,928,367, which is a continuation-in-part of Ser. No. 119,377, Feb. 26, 1971, abandoned, which is a continuation-in-part of Ser. No. 816,075, April 14, 1969, abandoned.

[52] U.S. Cl. .................. 260/294.8 C; 260/296 N; 260/295 N; 424/263

[51] Int. Cl.[2] ...................................... C07D 213/74

[58] Field of Search ............... 260/296 N, 294.8 C, 260/296 B, 295 N, 295.5 B

[56] References Cited

UNITED STATES PATENTS

| | | |
|---|---|---|
| 3,842,047 | 10/1974 | Williams et al. ............... 260/295 N |
| 3,843,663 | 10/1974 | Williams et al. ............... 260/295 N |

*Primary Examiner*—Alan L. Rotman
*Attorney, Agent, or Firm*—Stephen B. Coan; Raymond A. McDonald

[57] ABSTRACT

This invention relates to 1-amino naphthyridines prepared by a base-catalyzed condensation while in an aprotic solvent. In this condensation an o-alkyl aryl nitrile may be reacted either with the same or different o-alkyl aryl nitrile or with another nitrile. The 1-amino naphthyridines are useful as antifungal and antibacterial agents.

13 Claims, No Drawings

CERTAIN 8-AMINO-1,7-NAPHTHYRIDINES

This application is a divisional of our copending application, Ser. No. 379,525, filed July 16, 1973 now U.S. Pat. No. 3,928,367, which in turn, is a continuation-in-part of application Ser. No. 119,377, filed Feb. 26, 1971, now abandoned, which application in turn, is a continuation-in-part application of our copending application, Ser. No. 816,075, filed Apr. 14, 1969, now abandoned.

This invention relates to novel compositions of matter which may generically be described as 1-amino 3-substituted naphthyridines, to processes for their preparation and to their applied use characteristics as antibacterial and antifungal agents.

More particularly, this invention, in its composition of matter aspect, relates to 1-amino-2,5-naphthyridines, to 1-amino-2,6-naphthyridines, 1-amino-2,7-naphthyridines, to 8-amino-1,7-naphthyridines, each of said groups of naphthyrdidines being further substituted with such substituents as lower alkyl, phenyl, benzyl, phenethyl, pyridyl, thienyl, furyl, pyrazinyl, and pyrimidyl radicals.

In its process aspects this invention relates to the base-catalyzed condensation of an ortho-alkyl aryl nitrile either with itself or with another appropriate nitrile, said condensation taking place in an aprotic solvent.

In another of its process aspects, this invention relates to the application of the compositions of matter of this invention as antibacterial agents, said agents being utilized preferably in the form of the pharmaceutical formulations prepared consistent with skills well known and practiced by pharmaceutical artisans.

In another of its process aspects, this invention relates to the application of the compositions of this invention as antifungal agents, said agents being utilized preferably in the form of pharmaceutical formulations prepared consistent with skills well known by pharmaceutical artisans.

The compositions of matter of this invention may generically be depicted as naphthyridines having the structural formula:

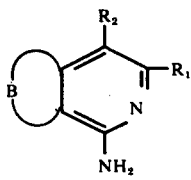

I wherein $R_1$ represents lower alkyl, phenyl, benzyl, phenethyl, thienyl, furyl, pyrazinyl, pyrimidyl, or pyridyl, $R_2$ represents hydrogen, lower alkyl, phenyl, benzyl, phenethyl and pyridyl, and B, together with the carbon atoms to which it is attached, is a pyrido moiety.

More conveniently, the naphthyridines may also be depicted by the following structural formulae:

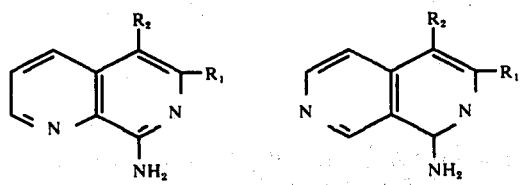

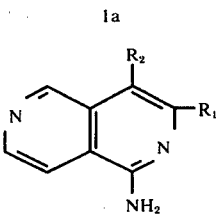 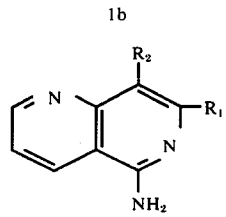

Ic.  Id wherein $R_1$ and $R_2$ are as defined for I, said structures Ia, Ib, Ic, and Id being 8-amino-1,7-naphthyridines, 1-amino-2,7-naphthyridines, 1-amino-2,6-naphthyridines, and 1-amino-2,5-naphthyridines, respectively.

Here, and elsewhere through this specification it will be understood that the phenyl, benzyl, thienyl, furyl, phenethyl, pyrazinyl, pyrimidinyl and pyridyl substitutents, as well as the pyrido moieties of the naphthyridine ring structures, can bear such other substitutents as would occur to a skilled organic chemist. Solely for illustration and without limitation, such substituents include lower alkyl, lower alkoxy, halo (chloro, bromo, iodo) nitro, lower alkylmercapto, trifluoromethyl and di(loweralkyl)amino and the like.

As used throughout this specification, the term "lower alkyl" means alkyl radicals having from one to six carbon atoms which can be arranged as straight or branched chains, and among which are, for purposes of illustration but without limiting the generally of the foregoing, methyl, ethyl, n-propyl, isopropyl, n-butyl, 2-butyl and n-hexyl.

The process aspect of this invention is carried out by condensing the appropriate reactants in the presence of a base which is in an atropic non-reactive solvent at temperatures of about −60° to about 80° C. More specifically, the process for preparing the compounds of this invention is essentially comprised of the condensation of an ortho-alkyl arylnitrile either with the same or different ortho-alkyl arylinitrile or with another type organic nitrile. In effecting the condensation the reactants are brought into contact with each other in the presence of a base; preferably, the reaction taking place in a solvent. In general, any atropic non-reacting solvent is suitable and such solvents include hydrocarbons, halohydrocarbons, tertiary amines, ammonia, ethers, tertiary amides, nitriles and the like, satisfying the requirements that they be liquid at reaction temperatures. Preferred solvents are dimethylformamide, dimethylsulfoxide, tetramethylurea, hexamethylphosphoramide, dioxane, tetrahydrofuran, dimethoxyethane, ether liquid ammonia, benzene, toluene and xylene. The bases generally found suitable for this reaction are the commonly used strong bases for alkylation reactions and include, potassium, t-butoxide, sodium t-amylate, sodium 2-methyl-2-butoxide, alkali metal amides such as sodium amide, potassium amide, lithium diethylamide, lithium diisopropylamide, sodium hydride, lithium hydride, triphenylmethyl lithium, triphenylmethyl sodium, naphthalene sodium and triphenylmethyl potassium. In general, the reactants are stirred together at temperatures in the range of about −60° to about 80° C, this temperature, of course, being dependent upon the solvent and speed of reaction desired. Preferably the reaction temperature is about 0° C, although more specific reactant/solvent/temperature/combination factors are described in the working examples set forth hereinbelow.

The nature of the general chemical reaction involved as well as of the general nature of the compounds formed may be illustrated as follows:

reactants are different, i.e., II and $R_1CN$ are not the same, the general structure of the reaction product is as given for formula I. In the latter situation condensation

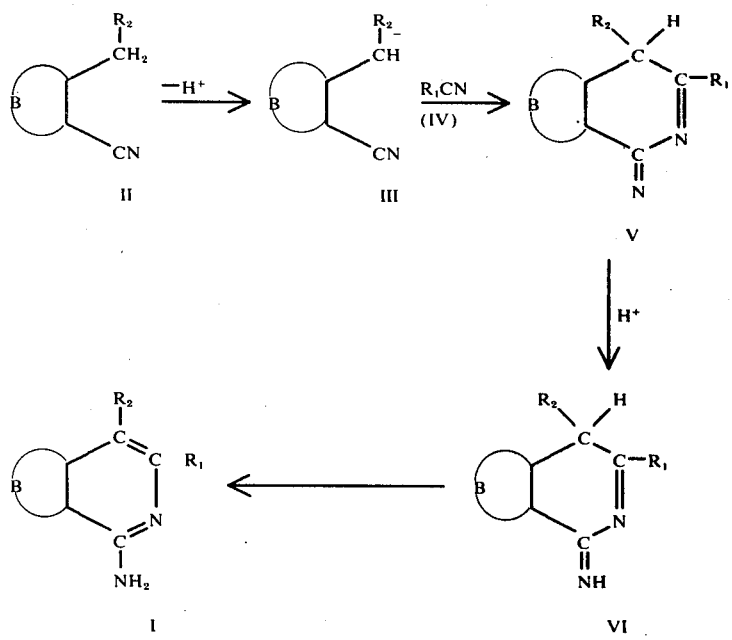

wherein B, $R_1$ and $R_2$ are as previously defined.

From the foregoing reaction scheme it becomes obvious that the second cyano molecule (IV) participating in the reaction (i.e. $R_1CN$) can either be identical with the ortho-alkyl aryl nitrol (II) molecule or different from it. In the first case the general structure of the product will be as follows:

between two molecules of the first component (II) can also take place as a side reaction. In such situations separation of the desired product may be accomplished by standard technique such as fractional crystallization and column chromatographic techniques.

It is also obvious from the reaction scheme that when different ortho-alkyl aryl nitriles are condensed, four different products may result therefrom. Such products may be represented as follows:

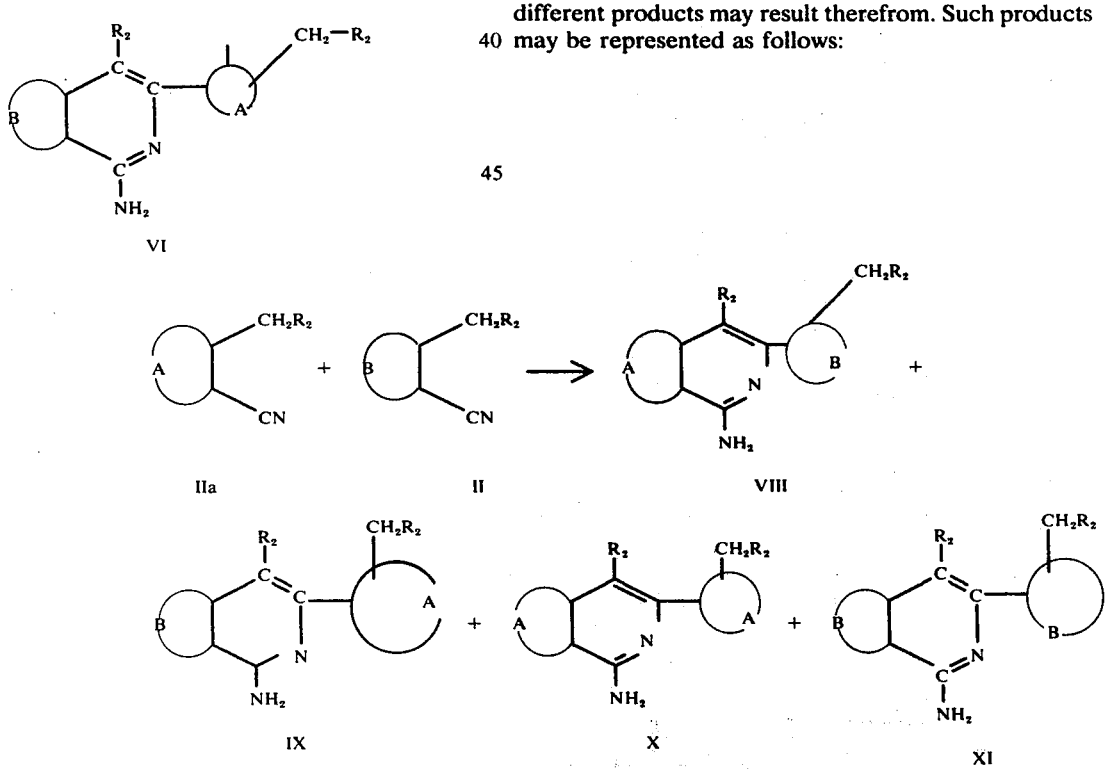

wherein $R_1$, $R_2$ and B are as previously described and A is a pyridyl radical. In the second situation wherein the wherein the "A" and "B" moieties represent different pyrido formations and $R_2$ is as defined in formula I. Again, in such situations separation of the desired product may be accomplished by standard techniques such as fractional crystallization and column chromatographic techniques. Representative of the organic nitriles (IV) suitable for reaction with the o-alkyl aryl nitriles of formula II are such compounds as 2-cyanopyridine, 3-cyanopyridine, 4-cyanopyridine, benzonitrile, o, m and p methoxy benzonitrile, 2,3-2,6- 3,4- and 3,5- dimethoxybenzonitrile, 3,4-methylenedioxyphenyl acetonitrile, o,m and p chlorobenzonitrile, trifluoromethyl benzonitrile, 1-and 2-naphthonitrile, benzylcyanide, o, m and p chlorobenzyl cyanide, o, m and p methylbenzyl cyanide, homoveratro nitrile, 4-methoxybenzyl cyanide, 2-cyano thiophene 2- and 3- thiophene acetonitrile, 2-cyanofurane, cyclobutyl cyanide, cyclopentyl cyanide, cyclohexyl cyanide and the like.

The following examples will further illustrate the process aspects for producing the tangible embodiments of the compounds of this invention.

EXAMPLE 1

Preparation of 1-amino-2,5-naphthyridines

1-Amino-3(2-methyl-3-pyridyl)2,5-naphthyridine

To 5.9 of 3-cyano-2-methylpyridine dissolved in 30 ml. of dimethylformamide, gradually add 6.7 g. of potassium t-butoxide at about 5° C. Maintain the mixture at 5° C for 4–6 hours and quench the reaction in ice water. Collect the crystalline precipitate and recrystallize from toluene to yield 1-amino-3(2-methyl-3-pyridyl)-2,5-naphthyridine.

In a similar manner by substituting the 3-cyano-2-methylpyridine with equivalent quantities of 3-cyano-2-ethylpyridine, 3-cyano-2-benzylpyridine, 3-cyano-2-phenethylpyridine and 3-cyano-2-phenylpropylpyridine and by substantially following the procedure of this example there is produced 1-amino-3(2-ethyl-pyridyl)-4-methyl-2,5-naphthyridine; 1-amino-3-(2-benzyl-3-pyridyl)-4-phenyl-2,5-naphthyridine; 1-amino-3-(2-benzyl-3-pyridyl)-4-phenyl-2,5-naphthyridine; 1-amino-3-(2-phenethyl-3-pyridyl)-4-benzyl-2,5-naphthyridine; 1-amino-3-(2-phenylpropyl-3-pyridyl)-4-phenethyl-2,5-naphthyridine, respectively. Similarly, in those instances wherein it is desired to produce those compounds bearing substituents on the pyridyl, phenyl and benzyl moieties of the foregoing then, as expected, the appropriately substituted starting reactants are then similarly reacted.

EXAMPLE II

1-Amino-3-methyl-2,5-naphthyridine

To 6.7 g. of potassium t-butoxide in dimethylformamide at 0–5° C add, in a portionwise fashion, 5.9 g. of 3-cyano-2-methylpyridine and stir the reaction mixture for 1 hour. Add in a portionwise fashion, 10.2 g. of acetonitrile and stir the reaction mixture at 0–5° C for 48 hours. Quench the reaction in ice water, filter the precipitate and recrystallize the desired 1-amino-3-methyl-2,5-naphthyridine from toluene.

In a similar manner by substituting the acetonitrile of the foregoing reaction with equivalent quantities of benzonitrile, benzylcyanide, phenpropionitrile, propionitrile, 2-cyanopyridine, 3-cyanopyridine, 4-cyanopyridine, 2-methoxybenzonitrile, 3-methoxybenzonitrile, 4-methoxybenzonitrile, 2,3-dimethoxybenzonitrile, 2,6-dimethoxybenzonitrile, 3,4-methylenedioxybenzonitrile, 2-chlorobenzonitrile, 3-chlorobenzonitrile, 4-chlorobenzonitrile, 2-trifluorobenzonitrile, 3-trifluorobenzonitrile, 4-trifluorobenzonitrile, 1-naphthonitrile, 2-naphthonitrile, 2-chlorobenzylcyanide, 3-chlorobenzylcyanide, 4-chlorobenzylcyanide, 2-methylbenzylcyanide, 3-methylbenzylcyanide and 4-methylbenzylcyanie, 4-methoxybenzylcyanide, 2-cyanothiophene, 2-thiopheneacetonitrile, 3-thiopheneacetonitrile, 2-cyanofuran, cyclobutylcyanide, cyclopentylcyanide, cyclohexylcyanide, 2-cyanopyrimidine, 5-cyanopyrimidine, 2-cyanopyrazine and by substantially following the foregoing reaction procedure there is produced 1-amino-3-phenyl-2,5-naphthyridine, 1-amino-3-benzyl-2,5-naphthyridine, 1-amino-3-phenethyl-2,5-naphthyridine, 1-amino-3-ethyl-2,5-naphthyridine, 1-amino-3-(2-pyridyl)-2,5-naphthyridine, 1-amino-3-(3-pyridyl)-2,5-naphthyridine, 1-amino-3-(3-pyridyl)-2,5-naphthyridine, 1-amino-3-(4-pyridyl)-2,5-naphthyrdine, 1-amino-3-(2-methoxyphenyl)-2,5-naphthyridine, 1-amino-3-(3-methoxyphenyl)-2,5-naphthyridine, 1-amino-3-(4-methoxyphenyl)-2,5-naphthyridine, 1-amino-3-(2,3-dimethoxyphenyl)-2,5-naphthyridine, 1-amino-3-(2,6-dimethoxyphenyl)-2,5-naphthyridine, 1-amino-3-(3,4-methylenedioxyphenyl)-2,5-naphthyridine, 1-amino-3-(2-chlorophenyl)-2,5-naphthyridine, 1-amino-3-(3-chlorphenyl)-2,5-naphthyridine, 1-amino-3-(4-chlorphenyl)-2,5-naphthyridine, 1-amino-3-(2-trifluoromethylphenyl)-2,5-naphthyridine, 1-amino-3-(3-trifluoromethylphenyl)-2,5-napthyridine, 1-amino-3-(4-trifluoromethylphenyl)-2,5-naphthyridine, 1-amino-3-(α-naphthyl)-2,5-naphthyridine, 1-amino-3-(β-naphthyl)-2,5-naphthyridine, 1-amino-3-(2-chlorobenzyl)-2,5-naphthyridine, 1-amino-3-(3-chlorobenzyl)-2,5-naphthyridine, 1-amino -3-(4-chlorobenzyl)-2,5-naphthyridine, 1-amino-3-(2-methylbenzyl)-2,5-naphthyridine, 1-amino-3-(3-methylbenzyl)-2,5-naphthyridine, 1-amino-3-(4-methylbenzyl)-2,5-naphthyridine, 1-amino-3-(4-methoxybenzyl)-2,5-naphthyridine, 1-amino-3-(2-thienyl)-2,5-naphthyridine, 1-amino-3-(2-thienylmethyl)-2,5-naphthyridine, 1-amino-3-(3-thienylmethyl)-2,5-naphthyridine, 1-amino-3-(2-furyl)-2,5-naphthyridine, 1-amino-3-cyclobutyl-2,5-naphthyridine, 1-amino-3-cyclopentyl-2,5-naphthyridine, 1-amino-3-cyclohexyl-2,5-naphthyridine, 1-amino-3-(2-pyrimidinyl)-2,5-naphthyridine, 1-amino-3-(3-pyrimidinyl)-2,5-naphthyridine, 1-amino-3-(2-pyrazinyl)-2,5-naphthyridine.

Similarly, by substituting the 3-cyano-2-methylpyridine reactant with equivalent quantities of 3-cyano-2-ethylpyridine, 3-cyano-2-benzylpyridine, 3-cyano-2-phenethylpyridine and by substantially following the foregoing reaction procedure there is produced 1-amino-3,4-dimethyl-2,5-naphthyridine, 1-amino-3-methyl-4-phenyl-2,5-naphthyridine, 1-amino-3-methyl-4-benzyl-2,5-naphthyridine, respectively. Similarly, in each of those reactions wherein the 3-cyano-2-methylpyridine has been substituted with another 3-cyano-2-substituted pyridine the acetonitrile reactant may also be substituted with the aforementioned nitriles and by substantially following the procedure described in the example, there is produced the appropriate 1-amino-3- and 4-substituted, 2,5-naphthyridines.

EXAMPLE III

Preparation of 1-amino-2,6-naphthyridines

1-Amino-3-(3-methyl-4-pyridyl)2,6-naphthyridine

To 5.9 g. of 4-cyano-3-methylpyridine dissolved in 30 ml. of dimethylformamide, gradually add 6.7 g. of potassium t-butoxide at about 5° C. Maintain the mixture at 5° C for 4 – t hours and quench the reaction in ice water. Collect the crystalline precipitate and recrystallize from toluene to yield 1-amino-3-(3-methyl-4-pyridyl)-2,6-naphthyridine.

In a similar manner by substituting the 4-cyano-3-methylpyridine with equivalent quantities of 4-cyano-3-ethylpyridine, 4-cyano-3-benzylpyridine, 4-cyano-3-phenethylpyridine and 4-cyano-3-phenylpropylpyridine and by substantially following the procedure of this example there is produced 1-amino-3-(3-ethyl-4-pyridyl)-4-methyl-2,6-naphthyridine, 1-amino-3-(3-benzyl-4-pyridyl)-4-phenyl-2,6-naphthyridine, 1-amino-3-(3-phenethyl-4-pyridyl)-4-benzyl-2,6-naphthyridine, 1-amino-3-(3-phenylpropyl-4-pyridyl)-4-phenethyl-2,6-naphthyridine, respectively. Similarly, in those instances wherein it is desired to produce those compounds bearing substituents on the pyridyl, phenyl or benzyl moieties of the foregoing then, as expected, the approximately substituted starting reactants are then reacted according to the procedure set forth in this example.

EXAMPLE IV

1-Amino-3-methyl-2,6-naphthyridine

To 6.7 g. of potassium t-butoxide in dimethylformamide at 0–5° C add, in a portionwise fashion, 5.9 g. of 4-cyano-3-methylpyridine and stir the reaction mixture for 1 hour. Add, in a portionwise fashion, 10.2 g. of acetonitrile and stir the reaction mixture at 0–5° C for 48 hours. Quench the reaction in ice water, filter the precipitate and recrystallize the desired 1-amino-3-methyl-2,6-naphthyridine.

In a similar manner by substituting the acetonitrile of the foregoing reaction with equivalent quantities of benzonitrile, benzylcyanide, phenpropionitrile, propionitrile, 2-cyanopyridine, 3-cyanopyridine, 4-cyanopyridine, 2-methoxybenzonitrile, 3-methoxybenzonitrile, 4-methoxybenzonitrile, 2,3-dimethoxybenzonitrile, 2,6-dimethoxybenzonitrile, 3,4-methylenedioxybenzonitrile, 2-chlorobenzonitrile, 3-chlorobenzonitrile, 4-chlorobenzonitrile, 2-trifluorobenzonitirile, 3-trifluorobenzonitirle, 4-trifluorobenzonitrile, 1-naphthonitrile, 2-naphthonitrile, 2-chlorobenzycyanide, 3-chlorobenzylcyanide, 4-chlorobenzylcyanide, 2-methylbenzycyanide, 3-methylbenzylcyanide, and 4-methylbenzycyanide, 4-methoxybenzylcyanide, 2-cyanothiophene, 2-thiopheneacetonitrile, 3-thiopheneacetonitrile, 2-cyanofuran, cyclobutylcyanide, cyclopentylcyanide, cyclohexylcyanide, 2-cyanopyrimidine, 5-cyanopyrimidine, 2-cyanopyrazine and by substantially following the foregoing reaction procedure there is produced 1-amino-3-phenyl-2,6-naphthyridine, 1-amino-3-benzyl-2,6-naphthyridine, 1-amino-3-phenethyl-2,6-napthyridine, 1-amino-3-ethyl-2,6-naphthyridine, 1-amino-3-(2-pyridyl)-2,6-naphthyridine, 1-amino-3-(3-puridyl)-2,6-naphthyridine, 1-amino-3-(4-pyridyl)-2,6-naphthyridine, 1-amino-3-(2-methoxy-phenyl)-2,6-naphthyridine, 1-amino-3-(3-methosyphenyl)-2,6-naphthyridine, 1-amino-3-(4-methoxyphenyl)-2,6-naphthyridine, 1-amino-3-(2,3-dimethoxyphenyl)-2,6-napthyridine, 1-amino-3-(2,6-dimethoxyphenyl)-2,6-napthyridine, 1amino-3-(2-chlorphenyl)-2,6-naphthyridine, 1-amino-3-(3-chlorphenyl)-2,6-naphthyridine, 1-amino-3-(4-chlorphenyl)-2,6-naphthyridine, 1-amino-3-(2-trifluoromethylphenyl)-2,6-naphthyridine, 1-amino-3-(3-trifluoromethylphenyl)-2,6-naphthyridine, 1-amino-3-(4-trifluoromethylphenyl)-2,6-naphthyridine, 1-amino-3-(α-naphthyl)-2,6-naphthyridine, 1-amino-3-(β-naphthyl)-2,6-naphthyridine, 1-amino-3-(β-naphthyl)-2,6-naphthyridine, 1-amino-3-(2-chlorobenzyl)-2,6-naphthyridine, 1-amino-3-(3-chlorobenzyl)-2,6-naphthyridine, 1-amino-3-amino-3-(4-chlorobenzyl)-2,6-naphthyridine, 1-amino-3-(2-methylbenzyl)-2,6-naphthyridine, 1-amino-3-(3-methylbenzyl)-2,6-naphthyridine, 1-amino-3-(4-methylbenzyl)-2,6-naphthyridine, 1-amino-3-(4-methoxybenzyl)-2,6-naphthyridine, 1-amino-3-(2-thienyl)-2,5-naphthyridine, 1-amino-3-(2-thienylmethyl)-2,6-naphthyridne, 1-amino-3-(3-thienylmethyl)-2,6-naphthyridine, 1-amino-3-(2-furyl)-2,6-naphthyridine, 1-amino-3-cyclobutyl-2,6-naphthyridine, 1-amino-3-cyclopentyl-2,6-naphthyridine, 1-amino-3-cyclohexyl-2,6-naphthyridine, 1-amino-3-(2-pyrimidinyl)-2,6-naphthyridine, 1-amino-3-(3-pyrimidinyl)-2,6-naphthyridine, 1-amino-3-(2-pyrazinyl)-2,6-naphthyridine.

Also by substituting the 4-cyano-3-methylpyridine with equivalent quantities of 4-cyano-3-ethylpyridine, 4-cyano-3-benzylpyridine, 4-cyano-3-propylpyridine, 4-cyano-3-phenethylpyridine, 4-cyano-3-phenylpropylpyridine and by substantially following the foregoing reaction procedure there is produced 1-amino-3,4-dimethyl-2,6-naphthyridine, 1-amino-3-methyl-4-phenyl-2,6-naphthyridine, 1-amino-3-methyl-4-benzyl-2,6-naphthyridine, 1-amino-3-methyl-4-phenethyl-2,6-naphthyridine, respectively. Also in each of those reactions wherein the 4-cyano-3-methylpyridine has been substituted with another 4-cyano-3-substituted pyridine, the acetonitrile reactant may also be substituted with the aforementioned nitriles and by substantially following the procedure described in this example there is produced the appropriately 1-amino-3- and 4-substituted 2,6-naphthyridines.

Preparation of 1-amino-2,7-naphthyridines

EXAMPLE V

1-Amino-3-(4-methyl-3-pyridyl)-2,7-naphthyridines

To 3 g. of 3-cyano-4-methylpyridine dissolved in 30 ml. of dimethylformamide, gradually add 3.4 g. of potassium t-butoxide at about 5° C over a period of 20 minutes. Maintain the reaction at 5° C and then at 20°–25° C for another 12 hours. Quench the reaction in ice water, collect the precipitate and recrystallize from ethanol-hexane to yield 1-amino-3-(4-methyl-3-pyridyl)-2,7-naphthyridine, m.p. 280°–282° C.

In a similar manner by substituting the 3-cyano-4-methylpyridine with equivalent quantities of 3-cyano-4-ethylpyridine, 3-cyano-4-benzylpyridine, 3-cyano-4-phenethylpyridine and 3-cyano-4-phenylpropylpyridine and by substantially following the procedure of this example there is produced 1-amino-3-(4-ethyl-3-pyridyl)-4-methyl-2,7-naphthyridine; 1-amino-3-(4-phenethyl-3-pyridyl)-4-phenyl-2,7-naphthyridine; 1-amino-3-(4-phenethyl-3-pyridyl)-4-benzyl-2,7-naphthyridine; 1-amino-3-(4-phenylpropyl-3-pyridyl)-4-phenethyl-2,7-naphthyridine, respectively. Similarly, in those instances wherein it is desired to produce those compounds bearing substituents on the pyrido, pyridyl, phenyl and benzyl moieties of the foregoing then, as expected, the appropriate substituted starting reactants are then similarly reacted.

EXAMPLE VI

1-Amino-3-methyl-2,7-naphthyridine

To 6.7 g. of potassium t-butoxide in dimethylformamide at 0°–5° C add, in a portionwise fashion, 5.9 g. of 3-cyano-4-methylpyridine and stir the reaction mixture for one hour. Add, in a portionwise fashion, 10.2 g. of acetonitrile and stir the reaction mixture at 0°–5° C for 48 hours. Quench the reaction in ice water, filter the precipitate and recrystallize the desired 1-amino-3-methyl-2,7-naphthyridine from toluene.

In a similar manner by substituting the acetonitrile of the foregoing reaction with equivalent quantities of benzonitrile, benzylcyanide, phenpropionitrile, propionitrile, 2-cyanopryridine, 3-cyanopyridine, 4-cyanopyridine, 2-methoxybenzonitrile, 3-methoxybenzonitrile, 4-methoxybenzonitrile, 2,3-dimethoxybenzonitrile, 2,6-dimethoxybenzonitrile, 3,4-methylenedioxybenzonitrile, 2-chlorobenzonitrile, 3-chlorobenzonitrile, 4-chlorobenzonitrile, 2-trifluorobenzonitrile, 3-trifluorobenzonitrile, 4-trifluorobenzonitrile, 1-naphthonitrile, 2-naphthonitrile, 2-chlorobenzylcyanide, 3-chlorobenzylcyanide, 4-chlorobenzylcyanide, 2-methylbenzylcyanide, 3-methylbenzylcyanide and 4-methylbenzylcyanide, 4-methoxybenzylcyanide, 2-cyanothiophene, 2-thiopheneacetonitrile, 3-thiopheneacetonitrile, 2-cyanofuran, cyclobutylcyanide, cyclopentylcyanide, cyclohexylcyanide, 2-cyanopyrimidine, 5-cyanopyrimidine, 2-cyanopyrazine and by substantially following the foregoing reaction procedure there is produced 1-amino-3-phenyl-2,7-naphthyridine, 1-amino-3-benzyl-2,7-naphthyridine, 1-amino-3-phenethyl-2,7-naphthyridine, 1-amino-3-ethyl-2,7-naphthyridine, 1-amino-3-(2-pyridyl)-2,7-naphthyridine, 1-amino-3-(3-pyridyl)-2,7-naphthyridine, 1-amino-3-(4-pyridyl)-2,7-naphthyridine, 1-amino-3-(2-methoxyphenyl)-2,7-naphthyridine, 1-amino-3-(3-methoxyphenyl)-2,7-naphthyridine, 1-amino-3-(4-methoxyphenyl)-2,7-naphthyridine, 1-amino-3-(2,3-dimethoxyphenyl)-2,7-naphthyridine, 1-amino-3-(2,6-dimethoxyphenyl)-2,7-naphthyridine, 1-amino-3-(3,4-methylenedioxyphenyl)-2,7-naphthyridine, 1-amino-3-(2-chlorophenyl)-2,7-naphthyridine, 1-amino-3-(3-chlorophenyl)-2,7-naphthyridine, 1-amino-3-(4-chlorphenyl)-2,7-naphthyridine, 1-amino-3-(2-trifluoromethylphenyl)-2,7-naphthyridine, 1-amino-3-(3-trifluoromethylphenyl)-2,7-naphthyridine, 1-amino-3-(4-trifluoromethylphenyl)-2,7-naphthyridine, 1-amino-3-(α-naphthyl)-2,7-naphthyridine, 1-amino-3-(β-naphthyl)-2,7-naphthyridine, 1-amino-3-(2-chlorobenzyl)-2,7-naphthyridine, 1-amino-3-(3-chlorobenzyl)-2,7-naphthyridine, 1-amino-3-(4-chlorobenzyl)-2,7-naphthyridine, 1-amino-3-(2-methylbenzyl)-2,7-naphthyridine, 1-amino-3-(3-methylbenzyl)-2,7-naphthyridine, 1-amino-3-(4-methylbenzyl)-2,7-naphthyridine, 1-amino-3-(4-methoxybenzyl)-2,7-naphthyridine, 1-amino-3-(2-thienyl)-2,7-naphthyridine, 1-amino-3-(2-thienylmethyl)-2,7-naphthyridine, 1-amino-3-(3-thienylmethyl)-2,7-naphthyridine, 1-amino-3-(2-furyl)-2,7-naphthyridine, 1-amino-3-cyclobutyl-2,7-naphthyridine, 1-amino-3-cyclopentyl-2,7-naphthyridine, 1-amino-3-cyclohexyl-2,7-naphthyridine, 1-amino-3-(2-pyrimidinyl)-2,7-naphthyridine, 1-amino-3-(3-pyrimidinyl)-2,7-naphthyridine, 1-amino-3-(2-pyrazinyl)-2,7-naphthyridine.

Similarly, by substituting the 3-cyano-4-methylpyridine reactant with equivalent quantities of 3-cyano-4-ethylpyridine, 3-cyano-4-benzylpyridine, 3-cyano-4-phenethylpyridine and by substantially following the foregoing reaction procedure there is produced 1-amino-3,4-dimethyl-2,7-naphthyridine, 1-amino-3-methyl-4-phenyl-2,7-naphthyridine, 1-amino-3-methyl-4-benzyl-2,7-naphthyridine, respectively. Similarly, in each of those reactions wherein the 3-cyano-4-methylpyridine has been substituted with another 3-cyano-4-substituted pyridine the acetonitrile reactant may also be substituted with the afore-mentioned niriles and by substantially following the procedure described in the example, there is provided the appropriate 1-amino-3- and 4-substituted 2,5-naphthyridine.

Preparation of 1,7-naphthyridine

EXAMPLE VII

8-Amino-2-(3-methyl-2-pyridyl)-1,7-naphthyridine

To 5.9 g. of 2-cyano-3-methylpyridine dissolved in 30 mls. of dimethylformamide gradually (20 minutes) add 6.7 g. of potassium t-butoxide at about 5° C. Maintain the reaction mixture at 5° C for 4–6 hours and quench the reaction mixture in ice water. Collect the crystalline precipitate and recrystallize from toluene obtaining 3.7 g. of 8-amino-2-(3-methyl-2-pyridyl)-1,7-naphthyridine, m.p. 170°–171° C.

EXAMPLE VIII

8-Amino-2-(3-ethyl-2-pyridyl)-3-methyl-1,7-naphthyridine

To 6.3 g. of 2-cyano-3-ethylpyridine (prepared from 3-ethylpyridine by the method described for the preparation of 2-cyano-6-methylpyridine from 2-methylpyridine in Organic Synthesis, Vol. 42, p. 30. The 2-cyano-3-ethylpyridine is separated from the 6-cyano and 4-cyano isomers by fractional crystallization from 2B-ethanol or isopropanol) dissolved in 30 mls. of dimethylformamide, gradually add 6.7 g. of potassium t-butoxide at about 5° C over a period of 20 minutes. Maintain the reaction mixture at 5° C for another 4–6 hours and then quench the reaction mixture in ice water. Collect the crystalline precipitate and recrystallize from toluene to yield 8-amino-2-(3-ethyl-2-pyridyl)-3-methyl-1,7-naphthyridine.

In a similar manner by substituting the 2-cyano-3-methyl-pyridine with equivalent quantities of 2-cyano-3-benzylpyridine, 2-cyano-3-phenethylpyridine and 2-cyano-3-phenylpropylpyridine and by substantially following the procedure of this example there is produced 8-amino-2-(3-benzyl-2-pyridyl)-3-phenyl-1,7-naphthyridine, 8-amino-2-(3-phenethyl-2-pyridyl)-3-benzyl-1,7-naphthyridine, 8-amino-2-(3-phenylpropyl-2-pyridyl)-3-phenethyl-1,7-naphthyridine, respectively. Similarly, in those instances wherein it is desired to produce those compounds bearing substituents on the pyridyl, phenyl and benzyl moieties of the foregoing then, as expected, the appropriately substituted starting reactants are then similarly reacted.

EXAMPLE IX

8-Amino-2-(3-methyl-2-pyridyl)-1,7-naphthyridine

To a suspension of sodamide (prepared from 0.23 g. of sodium) in 200 ml. of liquid ammonia gradually add 5.9 g. of 2-cyano-3-methylpyridine. Agitate the reaction mixture for 4 hours, add 6 g. of ammonium chloride and, using steam bath temperatures, evaporate off the ammonia. Add sufficient water to dissolve the inorganic material and filter the remaining precipitate which is recrystallized from toluene to give 8-amino-2-(3-methyl-2-pyridyl)-1,7-naphthyridine, m.p. 170°–171° C.

EXAMPLE X

8-Amino-2-(3-methyl-2-pyridyl)-1,7-naphthyridine

To a suspension in ether of lithium diisopropylamide (prepared from 0.2 moles of lithium, 0.1 moles of brombenzene and 0.1 moles of diisopropylamine) add, in a dropwise fashion, at 25°–35° C, an ether solution containing 0.1 mole of 2-cyano-3-methylpyridine. Reflux the reaction mixture for 7 hours, and pour the resulting mixture into ice water. Filter the precipitated 8-amino-2-(3-methyl-2-pyridyl)-1,7-naphthyridine and recrystallize the product from toluene.

EXAMPLE XI

8-Amino-2-methyl-1,7-naphthyridine

To 6.7 g. of potassium t-butoxide in dimethylformamide at 0.5° C add, in a portionwise fashion, 5.9 g. of 2-cyano-3-methylpyridine and stir the reaction mixture for 1 hour. Add, in a portionwise fashion, 10.2 g. of acetonitrile and stir the reaction mixture at 0.5° C for 48 hours. Quench the reaction in ice water, filter the precipitate and recrystallize the desired 8-amino-2-methyl-1,7-naphthyridine from toluene.

In a similar manner by substituting the acetonitrile of the foregoing reaction with equivalent quantities of benzonitrile, benzylcyanide, phenpropionitrile, propionitrile, 2-cyanopyridine, 3-cyanopyridine, 4-cyanopyridine, 2-methoxybenzonitrile, 3-methoxybenzonitrile, 4-methoxybenzonitrile, 2,3-dimethoxybenzonitrile, 2,6dimethoxybenzonitrile, 3,4-methylenedioxybenzonitrile, 2-chlorobenzonitrile, 3-chlorobenzonitrile, 4-chlorobenzonitrile, 2-trifluorobenzonitrile, 3-trifluorobenzonitrile, 4-trifluorobenzonitrile, 1-naphtonitrile, 2-naphtonitrile, 2-chlorobenzylcyanide, 3-chlorobenzylcyanide, 4-chlorobenzylcyanide, 2-methylbenzylcyanide, 3-methylbenzylcyanide and 4-methylbenzylcyanide, 4-methoxybenzylcyanide, 2-cyanothiophene, 2-thiopheneacetonitrile, 3-thiopheneacetonitrile, 2-cyanofuran, cyclobutylcyanide, cyclopentylcyanide, cyclohexylcyanide, 2-cyanopyrimidine, 5-cyanopyrimidine, 2cyanopyrazine and by substantially following the foregoing reaction procedure there is produced 8-amino-2-phenyl-1,7-naphthyridine, 8-amino-2-benzyl-1,7-naphthyridine, 8-amino-2-phenethyl-1,7-naphthyridine, 8-amino-2-ethyl-1,7-naphthyridine, 8-amino-2-(2-pyridyl)-1,7-naphthyridine, 8-amino-2-(3-pyridyl)-1,7-naphthyridine, 8-amino-2-(4-pyridyl)-1,7-naphthyridine, 8-amino-2-(2-methoxyphenyl)-1,7-naphthyridine, 8-amino-2-(3-methoxyphenyl)-1,7-naphthyridine, 8-amino-2-(4-methoxyphenyl)-1,7-naphthyridine, 8-amino-2-(2,3-dimethoxyphenyl)-1,7-naphthyridine, 8-amino-2-(2,6-dimethoxyphenyl)-1,7-naphthyridine, 8-amino-2-(3,4-methylenedioxyphenyl)-1,7-naphthyridine, 8-amino-2-(2-chlorophenyl)-1,7-naphthyridine, 8-amino-2-(3-chlorphenyl)-1,7-naphthyridine, 8-amino-2-(4-chlorphenyl)-1,7-naphthyridine, 8-amino-2-(2-trifluoromethylphenyl)-1,7-naphthyridine, 8-amino-2-(3-trifluoromethylphenyl)-1,7-naphthyridine, 8-amino-2-(4-trifluoromethylphenyl)-1,7-naphthyridine, 8-amino-2-($\alpha$-naphthyl)-1,7-naphthyridine, 8-amino-2-($\beta$-naphthyl)-1,7-naphthyridine, 8-amino-2-(2-chlorobenzyl)-1,7-naphthyridine, 8-amino-2-(3-chlorobenzyl)-1,7-naphthyridine, 8-amino-2-(4-chlorobenzyl)-1,7-naphthyridine, 8-amino-2-(2-methylbenzyl)-1,7-naphthyridine, 8-amino-2-(3-methylbenzyl)-1,7-naphthyridine, 8-amino-2-(4-methylbenzyl)-1,7-naphthyridine, 8-amino-2-(4-methoxybenzyl)-1,7-naphthyridine, 8-amino-2-(2-thienyl)-1,7-naphthyridine, 8-amino-2-(2-thienylmethyl)-1,7-naphthyridine, 8-amino-2-(3-thienylmethyl)-1,7-naphthyridine, 8-amino-2-(2-furyl)-1,7-naphthyridine, 8-amino-2-cyclobutyl-1,7-naphthyridine, 8-amino-2-cyclopentyl-1,7-naphthyridine, 8-amino-2-cyclohexyl-1,7-naphthyridine, 8-amino-2-(2-pyrimidinyl)-1,7-naphthyridine, 8-amino-2-(3-pyrimidinyl)-1,7-naphthyridine, 8-amino-2-(2-pyrazinyl)-1,7-naphthyridine.

Similarly, by substituting the 2-cyano-3-methylpyridine reactant with equivalent quantities of 2-cyano-3-ethylpyridine, 2-cyano-3-benzylpyridine, 2-cyano-3-phenethylpyridine and by substantially following the foregoing reaction procedure there is produced 8-amino-2,3-dimethyl-1,7-naphthyridine, 8-amino-2-methyl-3-phenyl-1,7-naphthyridine, 8-amino-2-methyl-3-benzyl-1,7-naphthyridine, respectively. Similarly, in each of those reactions wherein the 2-cyano-3-methylpyridine has been substituted with another 2-cyano-3-substituted pyridine the acetonitrile reactant may also be substituted with the aforementioned nitriles and by substantially following the procedure described in the example, there is produced the appropriate 8-amino-2- and 3-substituted 1,7-naphthyridine.

The compounds of this invention are useful as antifungal and antibacterial agents. In general, the potency of these compounds against a variety of bacteria and fungi by standard and conventional techniques such as with the use of standard disc assays. In general, the compounds are dissolved in 0.1N HCl and discs are dipped in appropriate concentrations to provide discs containing 200 or 20 mcg./disc. Bacteria were grown on nutrient agar, and were incubated at 37° C for 24 hours; yeasts were grown on Sabourauds agar and were incubated at 27° C for 48 hours; Trichophyton was grown on Mycosel agar and was incubated at 27° C for 4 days prior to measurement of inhibition zones. Typical of the results of the anti-bacerial and anti-fungal effects of the compounds of this invention are summarized by the results of 8-amino-2-(3-methyl-2-pyridyl)-1,7-naphthyridine in Table I. Tube dilution tests, using conventional techniques, are used to determine further in vitro potency of the compounds of this invention. Typical results are represented by the date of Table II.

Table I

Disc Testing of 8-amino-2-(3-methyl-2-pyridyl)-1,7-naphthyridine

| Organisms | 8-Amino-2-(3-methyl-2-pyridyl)-1,7-naphthyridine Inhibition Zone in mm. | |
|---|---|---|
| | 200 mcg. | 20 mcg. |
| Staphylococcus aureus 209P | 40 | ± |
| Streptococcus pyrogenes C | 27 | 0 |
| Escherichia coli | 30 | 0 |
| Pseudomonas aeruginosa | 30 | 0 |
| Salmonella schottmuelleri | 30 | ± |
| Candida albicans 404 | 12 | 0 |
| Candida albicans 420 | 30 | 0 |
| Candida albicans 406 | 0 | 0 |
| Candida albicans 12031 | 0 | 0 |
| Candida albicans 400 | 16 | 0 |
| Candida albicans 402 | 16 | 0 |
| Candida albicans 403 | 0 | 0 |
| Candida albicans 411 | ± | 0 |
| Saccharomyces cerevisiae | 20 | 0 |
| Trichophyton mentagrophytes | 40 | — |

Bacteria on nutrient agar, yeasts on Sabourauds agar and Trichophyton on Mycosel agar.

Table II

In Vitro Activity of 8-amino-2-(3-methyl-2-pyridyl)-1,7-naphthyridine by Tube Dilution

| Organisms | 8-Amino-2-(3-methyl-2-pyridyl)-1,7-naphthyridine |
|---|---|
| Staphylococcus aureus 209P | 25 |
| Streptococcus pyogenes C | 25 |
| Escherichia coli | 25 |
| Pseudomonas aeruginosa | 25 |
| Candida albicans 404 | 50 |
| Candida albicans 420 | 37.5 |
| Candida albicans 406 | 50 |
| Candida albicans 12031 | 50 |
| Candida albicans 400 | 37.5 |
| Candida albicans 402 | 50 |
| Candida albicans 403 | 50 |
| Candida albicans 411 | 37.5 |
| Saccharomyces cerevisiae | 37.5 |
| Trichophyton mentogrophytes | 0.75 |
| Trichophyton rubrum No. 3 | 17.5 |
| Trichophyton rubrum 14001 | 17.5 |
| Trichophyton rubrum Lyons | 25 |

Bacteria in yeast beef broth, fungi in Sabourauds dextrose broth

The compounds contemplated as falling within Formula I are basic in character and form acid addition salts. These salts sometimes increase solubility and lend themselves better to formulation than do the free bases. Accordingly, the pharmaceutically acceptable acid addition salts of the free bases are contemplated as being within the concept of its composition aspect. Such salts include those derived from maleic, salicylic, succinic, methyl sulfonic, tartaric, citric, hydrochloric, hydrobromic, sulfuric, phosphoric and the like, and are prepared by standard and well-known techniques.

In their function as therapeutically useful compounds, it is advantageous to administer the compounds to the host animal in admixture with an acceptable pharmaceutical carrier suitable for enteral or parenteral administration, said carrier constituting a major portion of the admixture. Such preparations may be in such forms as, for example, tablets, capsules and suppositories, or in liquid forms, as for example, elixirs, emulsions, sprays and injectables. In the formulation of pharamaceutical preparations there can be employed such substances which do not react with the active substance, as, for example, water, galatin, lactose, starches, magnesium stearate, talc, vegatable oils, benzyl alcohols, gums, polyalkylene glycols, petroleum jelly and the like.

The active ingredient of such pharmaceutical preparations is preferably present in the preparation in such proportions by weight that the proportion by weight of the active ingredient to be administered lies between 0.1 and 50%.

Representative embodiments of the formulations containing the compositions of this invention are as follows:

I TABLET FORMULATIONS
Enteric Coated Tablets

| Formula | mg./core |
|---|---|
| 8-Amino-2-(3-methyl-2-pyridyl)-1,7-naphthyridine | 100.0 |
| Citric acid | 1.0 |
| Lactose, U.S.P. | 33.5 |
| Dicalcium phosphate | 70.0 |
| Pluronic F-68 | 30.0 |
| Sodium Lauryl sulfate | 15.0 |
| Polyvinylpyrrolidone | 15.0 |
| Carbowax 1500 | 4.5 |
| Carbowax 6000 | 45.0 |
| 3A alcohol, 50 ml./1000 cores | |
| Corn starch | 30.0 |
| Dry: | |
| Sodium Lauryl Sulfate | 3.0 |
| Magnesium stearate | 3.0 |
| Tablet Weight | 350.0 |

Procedure — The 8-amino-2-(3-methyl-2-pyridyl)-1,7-naphthyridine is mixed with the citric acid, lactose, dicalcium phosphate, pluronic and sodium layryl sulfate. The above mixture is screened through a No. 60 screen and damp granulated with an alcoholic solution consisting of polyvinylpyrrolidone. Carbowax 1500 and 6000. Add additional alcohol, if necessary, to bring powders to a pasty mass. Add corn starch and continue mixing until uniform granules are formed. Pass through a No. 10 screen, tray and dry in oven at 100° C for 12 – 14 hours. Reduce dried granulation through a No. 16 screen, add sodium lauryl sulfate and magnesium sulfate, mix and compress into desired shape on a table machine.

Coating — The above cores are treated with a laccquer and dusted with talc to prevent moisture adsorption. Sub-coat layers are added to round out the core. A sufficient number of lacquer coats are applied to make the core enteric. Additional sub-coats and smoothing coats are applied to completely round out and smooth the tablet. Color coats are applied until desired shade is obtained. After drying the coated tablets are polished to give the tablets an even gloss.

II CAPSULE FORMULATIONS

| A. Formula | Mg./Capsule |
|---|---|
| 8-Amino-2-(3-methyl-2-pyridyl)-1,7-naphthyridine | 100.00 |
| Citric Acid | 1.00 |
| Pluronic, F-68 | 40.00 |
| Sodium lauryl sulfate | 20.00 |
| Lactose | 238.00 |
| Magnesium stearate | 1.00 |
| | 400.00 |

Procedure — Mix together 8-amino-2) -(3-methyl-2-pyridyl)-1,7-naphthyridine, citric acid, pluronic, sodium lauryl sulfate and lactose. Pass through a No. 80 screen. Add magnesium stearate, mix and encapsulate into the proper size 2-piece gelatin capsule.

| B. Formula | Mg./Capsule |
|---|---|
| 8-Amino-2-(3-methyl-2-pyridyl)-1,7-naphthyridine | 100.0 |
| Dried aluminum hydroxide gel | 100.0 |
| Citric acid | 1.0 |
| Pluronic, F-68 | 50.0 |
| Sodium lauryl sulfate | 25.0 |
| Lactose | 222.0 |
| Magnesium stearate | 2.0 |
| | 500.0 |

Procedure — Mix together 8-amino-2-(3-methyl-2-pyridyl)-1,7-naphthyridine, citric acid, pluronic, sodium lauryl sulfate and lactose. Pass through a No. 80 screen. Add magnesium stearate, mix and encapsulate into the proper size 2-piece gelatin capsule adding the dried aluminum hydroxide gel to the mixture before screening.

III ORAL SUSPENSION

| Formula | | |
|---|---|---|
| 8-Amino-2-(3-methyl-2-pyridyl)-1,7-naphthyridine | mg./5 ml. | 100.0 |
| Veegum, Vanderbilt | " | 50.0 |
| Standard granulated sugar, USP | " | 2500.0 |
| Sorbitol solution, USP | " | 1250.0 |
| Sodium saccharin, NF | " | 50.0 |
| Sodium benzoate, USP | " | 5.0 |
| Ethanol, USP | ml. | 0.025 |
| Menthol, USP | mg./5 ml. | 1.000 |
| Flavor | | Q.s. |
| Purified water, USP, to make 5 ml. | | |

Method of Manufacture — Dissolve the sodium saccharin, sodium benzoate, standard granulated sugar and sorbitol solution in approximately 80% of the required amount of water. Disperse the Veegum in approximately 5% of the required amount of water and add the dispersion to the previously prepared syrup. Prepare a slurry of the 8-amino-2-(3-methyl-2-pyridyl)-1,7-naphthyridine with approximately 10% of the required amount of the water and pass through a suitable colloid mill until free of grittiness. Add the milled active slurry to the batch. Dissolve the menthol and flavor in the alcohol and add the resulting solution to the batch. Add sufficient purified water to bring the batch to total volume. Agitate until uniform.

Additionally, the compounds of this invention are useful as antiobesity agents at dosage ranges of about 10–50 m.p.k. per day. In this end-use characteristic the compounds have demonstrated the ability to inhibit lipogenesis in adipose tissue as determined by administration of tracer doses of radioglucose together with an oral glucose level to male rats and the radioactivity in the epididymal fat pad is measured as an index of lipid synthesis. The test compound is administered one hour prior to the administration of the glucose. The active compounds decrease the radioactivity in the fat pad. Those compounds which are active in this test procedure, i.e. have the ability to decrease epididymal fat pad and body weights in male rats, are very useful as antiobesity agents.

Of particular interest in the class of naphthyridines of this invention are those compounds having in their 3-position a pyridyl radical. Of particular interest are 8-amino-2-(3-methyl-2-pyridyl)-1,7-naphthyridine, 8-amino-2-(3-methyl-4-pyridyl)-pyridyl)-1,7-naphthyridine and 8-N-methylamino-6-(3-methyl-2-pyridyl-1,7-naphthyridine.

In their use as antiobesity agents the compounds are administered in admixture with suitable pharmaceutical carriers such as those described hereinabove.

We claim:

1. a compound of the formula:

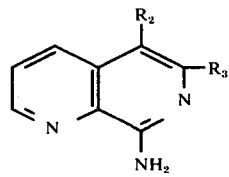

wherein $R_2$ is selected from the group consisting of hydrogen, lower alkyl, phenyl, benzyl, phenthyl and pyridyl and $R_3$ is selected from the group consisting of furyl and thienyl.

2. A compound of claim 1 wherin $R_3$ is thienyl.

3. A compound of claim 1 wherein $R_3$ is furyl.

4. A compound of claim 1 wherein $R_2$ represents hydrogen and $R_3$ is thienyl.

5. A compound of claim 1 wherein $R_2$ is lower alkyl and $R_3$ is thienyl.

6. A compound of claim 1 wherein $R_2$ is phenyl and $R_3$ is thienyl.

7. A compound of claim 1 wherein $R_2$ is pyridyl and $R_3$ is thienyl.

8. A compound of claim 1 wherein $R_2$ is hydrogen and $R_3$ is furyl.

9. A compound of claim 1 wherein $R_2$ is lower alkyl and $R_3$ is furyl.

10. A compound of claim 1 wherein $R_2$ is pyridyl and $R_3$ is furyl.

11. A compound of claim 4 wherein $R_2$ is hydrogen and $R_3$ is 2-thienyl, said compound being 8-amino-2-(2-thienyl)-1,7-naphthyridine.

12. A compound of claim 4 wherein $R_2$ is hydrogen and $R_3$ is 2-thienylmethyl, said compound being 8-amino-2-(2-thienylmethyl)-1,7-naphthyridine.

13. A compound of claim 8 wherein $R_2$ is hydrogen and $R_3$ is 2-furyl, said compound being 8-amino-2-(2-furyl)-1,7-naphthyridine.

* * * * *